United States Patent [19]

Shanbrom et al.

[11] 4,189,425

[45] Feb. 19, 1980

[54] METHOD OF PRESERVING BLOOD PLASMA I

[75] Inventors: Edward Shanbrom, Santa Ana; Robert C. Bishop, Los Angeles, both of Calif.

[73] Assignee: Edward Shanbrom, Inc., Santa Ana, Calif.

[21] Appl. No.: 914,354

[22] Filed: Jun. 12, 1978

Related U.S. Application Data

[63] Continuation of Ser. No. 796,924, May 16, 1977, Pat. No. 4,105,650, and a continuation of Ser. No. 567,372, Apr. 11, 1975, abandoned.

[51] Int. Cl.$^2$ ............................................. A61K 37/02
[52] U.S. Cl. ................................................. 260/112 B
[58] Field of Search ...................................... 260/112 B

[56] References Cited

U.S. PATENT DOCUMENTS

| 3,652,530 | 3/1972 | Johnson | 260/112 B |
| 3,770,631 | 11/1973 | Fekete | 260/112 B |
| 4,073,886 | 2/1978 | Kehm | 260/112 B |

*Primary Examiner*—Paul R. Michl
*Attorney, Agent, or Firm*—Knobbe, Martens, Olson, Hubbard & Bear

[57] ABSTRACT

Polyethylene glycol or poly(oxyethylene)poly(oxypropylene) glycol block copolymers or mixtures thereof in a suitable buffer such as citrated saline, are added to blood plasma to preserve and protect blood coagulation factors and other proteins.

1 Claim, No Drawings

METHOD OF PRESERVING BLOOD PLASMA I

This is a continuation of application Ser. No. 567,372 filed Apr. 11, 1975, now abandoned, and application Ser. No. 796,924, filed May 16, 1977 now U.S. Pat. No. 4,105,650, issued Aug. 8, 1978.

RELATED PATENTS AND APPLICATIONS

Application Ser. No. 567,371, filed Apr. 11, 1975, entitled METHOD OF PRESERVING BLOOD PLASMA II, now abandoned. Application Ser. No. 797,108, filed May 16, 1977, entitled METHOD OF PRESERVING BLOOD PLASMA II, issued Apr. 25, 1978, U.S. Pat. No. 4,086,216. Application Ser. No. 834,346, filed Sept. 19, 1977, entitled METHOD OF PRESERVING BLOOD PLASMA II, now U.S. Pat. No. 4,137,223.

BRIEF SUMMARY OF THE INVENTION

Plasma constituents are preserved and protein fractions, for example blood coagulation factors, such as anti-hemophilic factor (AHF, Factor VIII), are thus produced in greater yield by mixing plasma or plasma fractions with a preservative solution which comprises a buffer, for example citrated saline solution, containing either polyethylene glycol or a block copolymer poly(oxyethylene)poly(oxypropylene) glycol, sold under the trademark PLURONIC, or mixtures of the same.

BACKGROUND

Background information concerning various aspects of this invention may be found in the patents and publications incorporated in this disclosure by reference and listed at the end of the specification. The parenthetical numerals appearing in the following discussion refer to the respective patents and publications.

The process of blood coagulation is an important activity which normal, whole blood is capable of carrying out under timely circumstances to prevent excessive loss of blood through open wounds or by internal bleeding. It is known that normal whole blood contains a factor which is absent, or seriously deficient in hemophiliacs. This factor is associated with the globulin fraction of blood and has come to be known as antihemophilic factor, AHF, FACTOR VIII, or AHG.

Scientists have known about AHF and its role in blood coagulation for some time, and the treatment of hemophilia heretofore has generally consisted of replacement therapy whereby the patient is transfused with many pints of fresh whole blood or specially prepared plasma.

It is known, however, that under ordinary storage conditions whole blood and liquid plasma begin rapidly to lose their AHF activity in a day or so. While it is possible to freeze and store fresh plasma, AHF activity in frozen plasma may also decrease with time. It is possible to reduce this loss of AHF activity by storing or drying freshly frozen plasma, but it is desirable to have a source of AHF of known strength and increased potency.

Many methods of isolation or concentration of AHF for the preparation of plasma fractions rich in AHF from human or animal blood have been made, and certain methods have been developed which are reliable, in that AHF activity of a desired concentration has been produced.

The preparation of cryoprecipitate and the concentration of AHF in this material is known (16). Cryoprecipitate concentrate refers to the precipitate obtained from the freezing and cold thawing of human or animal blood plasma, and separated from the supernatant fraction of the plasma. The cryoprecipitate concentrate is preferably obtained by the rapid freezing of fresh plasma, although stored plasma can also be used. The freezing is usually carried out at temperatures from about $-20°$ C. to about $-40°$ C., followed by slow thawing at about $4°$ C. Many precipitating agents for AHF are known. These include ethanol, ethyl ether, ammonium sulphate, phosphate-sodium citrate, amino acids, glycine, and others (16).

One of the important precipitating agents for AHF is a substance known as polyethylene glycol, abbreviated as PEG. Polyethylene glycol is obtained by the polymerization of ethylene oxide in the presence of ethylene glycol (Ref. 1; Vol. 10, pp. 638–676). Polyethylene glycols, also known as poly(oxyethylene) are prepared in various molecular weights ranging from the liquid polyethylene glycols having a molecular weight of from about 200 to about 600 and the solid polyethylene glycols having molecular weights from about 900 to about 8,000, with paste-like materials is between about 600 and 900. Polyethylene glycols are sold by Union Carbide under the name CARBOXWAX and UCON, the latter being a liquid product.

Closely related to polyethylene glycol chemically and in properties are the polypropylene glycols and the mixed polyethylene-polypropylene glycols, the latter being block copolymers of ethylene oxide and propylene oxide, a large group of which are sold under the trade name PLURONIC, by BASF Wyandotte Chemical Company. (1; Vol. 10, pp. 658–659 and Ref. 2). These classes of compounds are known for their detergency and for their lack of toxicity (1,2) and both have been studied quite extensively in biological systems.

Polson studied the use of polyethylene glycol for the purification of proteins (9) and fractionation of blood plasma (10, 11, 12). Extensive studies on the use of PEG and other polyols intravenously have been conducted (13, 17, see also 2-8). The effect of PEG on AHF concentrates has been studied quite extensively and there have been a number of improved blood fractionation procedures (14, 15) including a procedure for preparing a stable high potency human AHF concentrate using PEG and glycine to fractionate a cryoprecipitate of AHF concentrate (16). PLURONIC polyols, because of their close chemical structure, their known lack of toxicity (1), and their proven compatibility with cells (3–6) make this class of compounds an obvious substitute for PEG in plasma fractionation procedures where PEG has been successfully used.

A number of advantageous features respecting this invention flow from the discovery that if a polyol, such as polyethylene glycol or a PLURONIC polyol or combination of these, are combined with plasma before freezing to produce cryoprecipitate, blood factors such as AHF and other plasma proteins, are preserved and greatly increased yields can be obtained and a product of greater stability and higher potency can be obtained than has been available in the prior art. PEG, or an equivalent polyol such as poly(oxyethylene)poly(oxypropylene) glycol block copolymer preserves and significantly increases the yield of AHF during cryoprecipitation and subsequent fractionation.

AHF recovery depends to a significant extent upon the temperatures utilized in the concentration process. While it is obviously convenient to operate at or near room temperature, prior art room temperature process steps had to be carried out very quickly because AHF degrades very rapidly at room temperature and always involves significant loss of AHF. The preservative effect polyol (PEG or PLURONIC polyol) is particularly important in processes in which the plasma fraction, including whole plasma, is processed at or near room temperature or when processing of the plasma fraction is prolonged. Unlike the prior art in which losses increase with increasing processing time, processing time becomes of secondary importance once the preservative effect of the present invention has been achieved.

The present invention is an improvement in the process of collecting and concentrating blood coagulation factors, wherein blood plasma is frozen and then thawed for further concentration or use.

The invention comprises adding a material selected from the group consisting of polyethylene glycol and alpha-hydroxy-omega-hydroxy-poly(oxyethylene)-poly(oxypropylene)poly(oxyethylene) block copolymer or mixtures of the same to whole, fresh blood plasma before freezing.

One feature of this invention is that AHF and other blood factors are preserved by adding a preservative solution to plasma followed by freezing and recovery or cryoprecipitate. Therapeutic agents for replacement therapy in hemophilia can thus be manufactured in higher yields when the preservative solution is used.

Another feature of the invention is that there is provided a preservative solution which consists essentially of either polyethylene glycol or alpha-hydroxy-omega-hydroxy-poly(oxyethylene)poly(oxypropylene)-poly(oxyethylene) copolymer, or both in a suitable buffer solution such as a citrated saline solution.

A related feature of the invention is that the preservative solution can be used to great advantage by mixing the preservative solution with plasma soon after collection to preserve the AHF and/or other protein constituents of the plasma. The plasma is frozen and when cold thawed, the cryoprecipitate therefrom may be used as a source of AHF and other constituents.

In one of its more important usages, the invention may be described similarly as a process of concentrating blood coagulation factors from blood plasma which includes the steps of freezing the blood plasma to obtain a cryoprecipitate fraction, separating the cryoprecipitate fraction from the bulk of the plasma, and concentrating the blood coagulation factors in the fraction by precipitation and dissolution steps which is improved by adding a preservative solution to the blood plasma before freezing. The preservative solution consists essentially of a polyol selected from a group consisting of polyethylene glycol and a PLURONIC polyol of the class alpha-hydroxy-omega-hydroxy-poly(oxyethylene)poly(oxypropylene) poly(pxyethylene) block copolymers, or mixtures of these polyols. Following this step, the plasma fraction may be handled in any conventional manner and the AHF may be concentrated in any conventional manner, such as by fractionation with alcohol, glycine and PEG, etc.

In the preferred embodiment, the method includes adding the preservative solution to plasma immediately upon collection, then causing the formation of cryoprecipitate by freezing and cold thawing the preserved plasma. That cryoprecipitate may be used directly or further processed to produce AHF concentrates.

Various facets features and advantages of the invention are detailed methods for carrying out the invention, can best be illustrated by example. It is to be understood, however, that examples are given merely to illustrate the invention and are not intended to limit the scope of the invention, which is defined by the claims and which will include a reasonable range of equivalents insofar as the particular steps and materials are concerned.

EXAMPLE I

The whole blood plasma fraction, and particularly the coagulation factors AHF and fibrinogen, and other constituents, are preserved, stabilized and thus obtained in increased yield by the addition of a preservative solution consisting essentially of a buffer solution containing PEG or PLURONIC polyol or both to the plasma, followed by freezing and thawing to produce cryoprecipitate. The final mixture of plasma and preservative solution should contain from about 0.1 gram to about 25 grams of polyol per liter of final mixture.

An exemplary preservative solution contains, per liter, 6.4 grams sodium chloride, 5.9 grams sodium citrate-dihydrate, 7.5 grams glycine and 250.0 grams polyethylene glycol 4,000.

PEG-4,000 is preferred but PEG having molecular weights from about 600 to about 10,000 are satisfactory. Solid, paste or liquid PLURONIC polyols which are soluble in water may be used in place of PEG. PLURONIC F38 polyol having a poly(oxypropylene) molecular weight of about 950 and a poly(oxyethylene) content of about 80% is preferred, but polyols of this class having a poly(oxyethylene) content of as low as 10% may be used provided the poly(oxypropylene) molecular weight is low, less than about 1,750. Generally, the poly(oxyethylene) content should be about 20% or higher and the poly(oxypropylene) molecular weight should be from about 900 to about 4,000. Reference No. (2) gives extensive information respecting the selection of PLURONIC polyols for various purposes.

About 10 milliliters of the preservative solution is placed in a suitable plasma pooling container and then about 500 milliliters of plasma added. After gentle agitation to insure complete mixing, the preserved plasma is placed at between $-20°$ C. and $-50°$ C. to effect rapid freezing. Once frozen, the plasma is placed at between $+2°$ C. and $+4°$ C. for cold thawing to produce cryoprecipitate. The cryoprecipitate is then either dissolved and used directly or further processed to produce AHF concentrate.

The yield of the AHF recovered in the processes of the prior art is typically in the range of about 35%. By carrying out the concentration of AHF according to the foregoing process, the yield of blood coagulation factors has been increased to approximately 50%. This increase yield results primarily from the stabilizing effect of the polyol upon those proteins and protein complexes precipitated by the freeze and cold thaw technique. Because they are stabilized and thus less susceptible to destruction by the cryoprecipitation process itself, a substantially larger amount of cryoprecipitate is obtained by this method.

The exact mechanism by which the polyol preserves the AHF is not known. Whatever the mechanism, the process gives results not predictable from the prior art. An apparent synergistic protective effect results from polyol in combination with heparin, see our application filed concurrently herewith.

In the preceding example, a number of specific materials and solutions have been described in order to present the best mode known of carrying out the invention. It will be understood that no special importance is attached to the nature of the buffer solution, citrated saline being only well known and an example of suitable buffers. Other buffers include phosphate buffers, glycine buffers, imidazole buffers, etc., which are standard biochemical buffer solution. It is, of course, not necessary and not feasible to list all of the known equivalents of each of the materials, but it is within the scope of the invention to substitute one or more equivalent materials for the specific materials referred to as exemplary in the specification.

Variations in procedure and technique are also permitted within the present invention. For example, removal of the polyol, PEG or PLURONIC polyol can be accomplished by ultrafiltration, dialysis, reverse osmosis or by precipitation with alcohol, glycine or other equivalent materials. Usually this is not essential and, accordingly, this step is not made an integral part of the procedure.

There are a number of important advantages to the foregoing invention, including but not limited to the following:

Higher yields are attainable because of the preservative effect of the inventive solutions. Processing at room temperature and above is permitted without serious decrease of yield. The process may be carried out in phases, e.g., part of the process can be carried out one day and the remainder carried out the next day, because AHF degeneration has been inhibited by the preservative solution.

There are other advantages, some of which are referred to hereinbefore, which will be appreciated by those familiar with the complexities of the prior art which result from the invention as defined in the claims appearing hereinafter.

Disclosures Incorporated by Reference

The disclosure of the following patents and publications is incorporated into the disclosure of this patent by reference:

1. Kirk-Othmer *ENCYCLOPEDIA OF CHEMICAL TECHNOLOGY,* 2nd Ed., John Wiley & Sons, New York (1966).

2. The Wonderful World of Pluronic Polyols, BASF Wyandotte Corporation, Wyandotte, Mich. (1971).

3. *Induced Permability Changes in Reconstituted Cell Membrane Structure,* Seufert, W. D., Nature 207, 174 (1965).

4. *Biologie Cellulaire—Comportement Osmotique des hematies dans des solution d'un detergent non ionique; le* Pluronic F68, Roze, C., C. R. Acad. Sci. 263, 1615 (1966).

5. *Physiologie Cellulaire—Comportement osmotique des hamaties dans des solutions de 3 polymeres hydrophiles: polyoxyethylene-glycol* 6000, polyvinylpyrrolidine 1100 et Pluronic F68, Roze C., C. R. Acad. Sci. 266, 508 (1968).

6. *Effect of Pluronic F68* on Blood Coagulation, Nalbandian, R. M. et al, Bull. of Pathal. 10, 90 (1969).

7. U.S. Pat. No. 3,089,818, May 14, 1963.

8. U.S. Pat. No. 3,457,348, July 22, 1969.

9. *Polyethylene Glycol in Purification of Proteins and Other High Molecular Weight Substances,* A, Polson, Hemophelia A.

10. U.S. Pat. No. 3,415,804, Dec. 10, 1968.

11. *Fractionation of Plasma with Polyethylene Glycol,* A. Polson & C. Ruiz-Bravo, Vox, Sang. 23:107–118 (1972).

12. *The Fractionation of Protein Mixtures by Linear Polymers of High Molecular Weight,* A. Polson et al, Biochem. Biophys. Acta S2 pp. 463–475 (1964).

13 *Clinical Investigation of Intermediate and High-Purity Antihaemophilic Factor (Factor VIII) Concentrates,* A. J. Johnson et al, British Journal of Haematology, (1971).

14. U.S. Pat. No. 3,763,135, Oct. 2, 1973.

15 U.S. Pat. No. 3,560,476, Feb. 2, 1971.

16. U.S. Pat. No. 3,631,018, Dec. 28, 1971.

17. *Flurocarbon-Polyol Artificial Blood Substitutes,* R. P. Geyer, N-Eng. J. of Med. 289:1077, 1973.

We claim:

1. The method of preserving blood plasma coagulation factors and other proteins during freezing and thawing of plasma for improving the recovery of coagulation of proteins thereafter comprising the steps of:
    (a) adding to whole, fresh blood plasma a preservative solution consisting essentially of alpha-hydroxy-omega-hydroxy-poly(oxyethylene)poly(oxypropylene)poly(oxyethylene) block copolymer or mixtures of the same with polyethylene glycol to a concentration of from about 0.1 to about 25 grams of polyol per liter of plasma;
    (b) thereafter freezing the blood plasma containing said preservative; and
    (c) thereafter thawing the frozen blood plasma containing the preservative solution to recover therefrom plasma cryoprecipitate from which plasma proteins can be recovered in improved yield.

* * * * *